United States Patent [19]

Hall et al.

[11] Patent Number: 4,608,386
[45] Date of Patent: Aug. 26, 1986

[54] 7-OXABICYCLOHEPTANE ETHERS USEFUL IN THE TREATMENT OF THROMBOTIC DISEASES

[75] Inventors: Steven E. Hall, Ewing Township, Mercer County; Wen-Ching Han, Trenton, both of N.J.

[73] Assignee: E. R. Squibb & Sons, Inc., Princeton, N.J.

[21] Appl. No.: 727,965

[22] Filed: Apr. 26, 1985

[51] Int. Cl.$^4$ ............... A61K 31/335; A61K 31/557; C07D 307/00
[52] U.S. Cl. ..................................... 514/469; 549/463
[58] Field of Search ........................ 549/463; 514/469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |
| 4,474,803 | 10/1984 | Hall | 549/463 |

FOREIGN PATENT DOCUMENTS 0043292 8/1982 European Pat. Off. .
2039909 8/1980 United Kingdom .

OTHER PUBLICATIONS

Hall et al., Chem. Abstracts, vol. 102, 131806q, (1985)–Abstract of Ger. Offen. DE 3,409,124, Sep. 1984.

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted ether prostaglandin analogs are provided having the structural formula

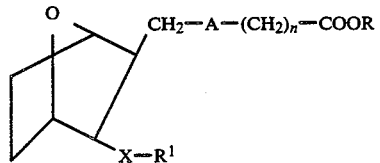

wherein X is O or

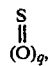

and including all stereoisomers thereof.

The compounds are cardiovascular agents useful, for example, in the treatment of thrombotic disease.

14 Claims, No Drawings

7-OXABICYCLOHEPTANE ETHERS USEFUL IN THE TREATMENT OF THROMBOTIC DISEASES

DESCRIPTION OF THE INVENTION

The present invention relates to 7-oxabicycloheptane substituted ether prostaglandin analogs which are cardiovascular agents useful, for example, in the treatment of thrombotic disease. These compounds have the structural formula

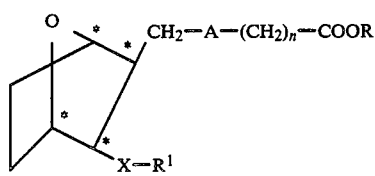   I and including all stereoisomers thereof, wherein
A is —CH=CH— or —(CH$_2$)$_2$,
n is 0 to 8,
X is O or

wherein q is 0, 1 or 2;
R is H, lower alkyl, alkali metal, or a polyhydroxylamine salt such as tris(hydroxymethyl)amino methane or glucamine and
R$^1$ is lower alkyl, aryl, aralkyl, cycloalkyl, cycloalkylalkyl, lower alkenyl or lower alkynyl.

Thus, the compounds of the invention include the following types of compounds:

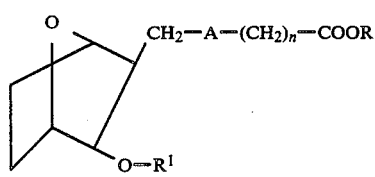   IA

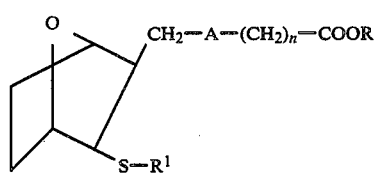   IB

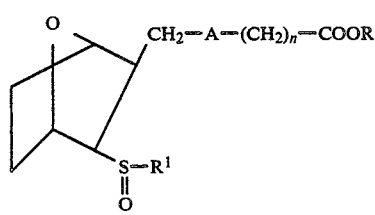   IC

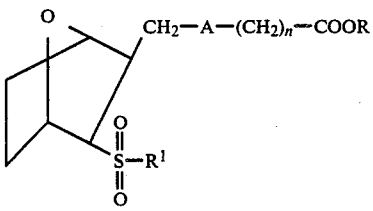   ID

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkyl-aryl substituent, a haloaryl substituent, a cycloalkyl substituent, an alkylcycloalkyl substituent, hydroxy, an alkylamino substituent, or an alkylthio substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups, an aryl group, 1 or 2 hydroxy groups, 1 or 2 alkylamino groups, or 1 or 2 alkylthio groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent or either the phenyl or naphthyl may be 1 or 2 lower alkyl groups, 1 or 2 halogens (Cl, Br or F), an aryl group, 1 or 2 lower alkoxy groups, 1 or 2 hydroxy groups, 1 or 2 alkylamino groups, or 1 or 2 alkylthio groups.

The term "aralkyl", "aryl-alkyl" or "aryl-lower alkyl" as used herein by itself or as part of another group refers to lower alkyl groups as discussed above having an aryl substituent, such as benzyl.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The term "halogen" or "halo" as used herein by itself or as part of another group refers to chlorine, bromine, fluorine or iodine, with chlorine being preferred.

The term "(CH$_2$)$_n$" includes a straight or branched chain radical having 1 to 8 carbons in the normal chain and may contain one or more lower alkyl or halo substituents. Examples of (CH$_2$)$_n$ groups include

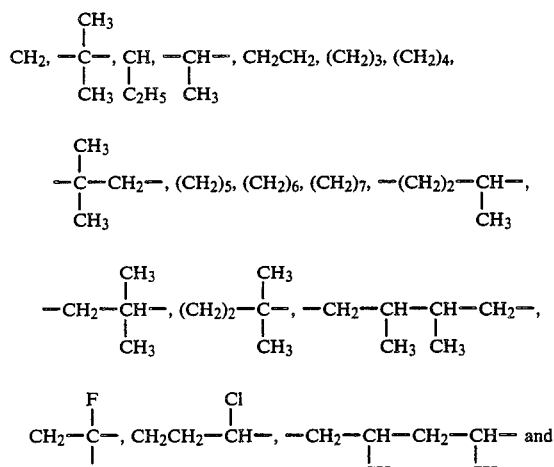

the like.

Preferred are those compounds of formula I wherein A is —CH=CH— or —CH$_2$—CH$_2$—, n is 3 to 5, X is O or S, R is H, and R$^1$ is lower alkyl, such as hexyl, aryl, such as phenyl, or aralkyl such as benzyl.

The various compounds of the invention may be prepared as outlined below.

Compounds of formula I wherein X is O may be prepared as follows.

The lactone A

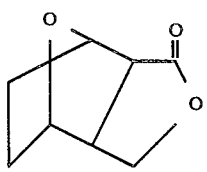

is treated with methyl lithium in the presence of an inert organic solvent, such as tetrahydrofuran, under argon, at reduced temperatures of from about −50° to about −30° C. to form the corresponding hemiketal B

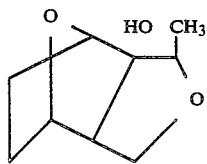

The hemiketal B is then subjected to silylation wherein hemiketal B in solution (such as with tetrahydrofuran) is treated with imidazole and t-butyldimethylsilyl chloride to form the corresponding cis ketone C

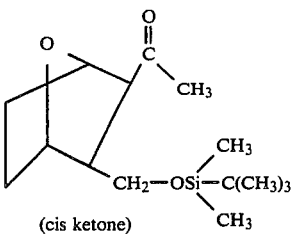

(cis ketone)

The cis ketone C may be used in the next step or may be epimerized to the corresponding trans ketone by reacting C with methyl alcohol and sodium methoxide under an inert atmosphere, such as argon, to form the trans silyloxy compound D which may be used in the next step

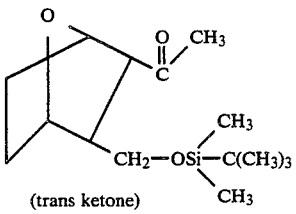

(trans ketone)

The cis ketone C or trans ketone D is oxidized by reaction with hydrogen peroxide and trifluoroacetic anhydride in methylene chloride in the presence of Na$_2$HPO$_4$ to form the corresponding trifluoroacetyl compound E

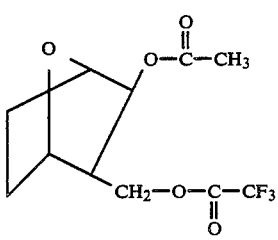

which is dissolved in tetrahydrofuran and treated with sodium bicarbonate solution to remove the trifluoroacetyl group and form the alcohol F

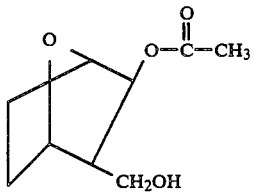

The alcohol F is then treated with 2-methoxyethoxymethyl chloride to form the hydroxy-protected compound G

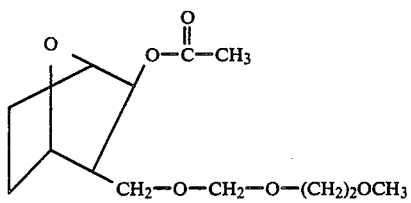
G

Where in the compounds of the invention of formula I, X, which is directly attached to the ring, is to be oxygen, then compound G is converted to the appropriate lower side chain group $R^1$ by treating G with strong base such as sodium hydroxide or potassium hydroxide in the presence of an inert solvent such as xylene and a mesylate of the structure MesylO—$R^1$   H to form the protected compound J

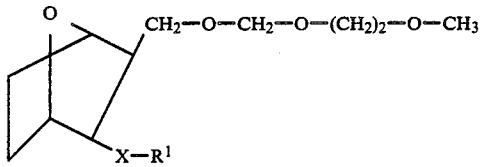
J (where X is O)

The corresponding alcohol is next formed by treating J with titanium tetrachloride in the presence of methylene chloride at reduced temperatures to form the alcohol K

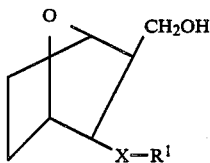
K which is then oxidized to the aldehyde L by treating K with pyridinium chlorochromate in the presence of methylene chloride and sodium acetate

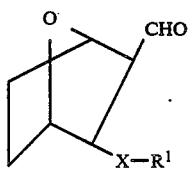
L

The aldehyde L is then subjected to a Wittig reaction by treating L with methoxymethylenetriphenyl phosphonium chloride in the presence of potassium t-amylate and an inert solvent such as tetrahydrofuran to form the vinyl ether compound M

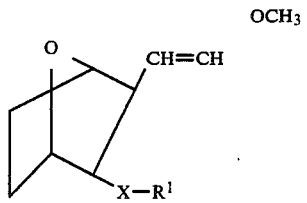
M

Vinyl ether M is then hydrolyzed by treating M with trifluoroacetic acid in the presence of an inert solvent such as tetrahydrofuran to form the aldehyde N

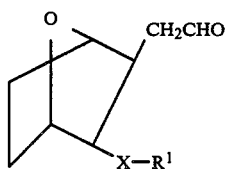
N which is subjected to a Wittig reaction by treating aldehyde N with the reaction product of carboxyalkyltriphenyl phosphonium bromide $(Br(C_6H_5)_3P(CH_2)_nCOOH)$ and potassium t-amylate and subsequently with diazomethane to form the methyl ester IE

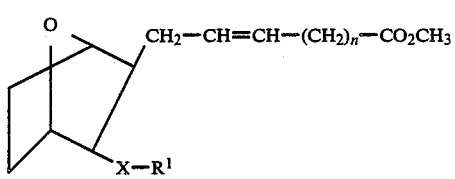
IE

The ester IE may then be hydrolyzed to the corresponding acid IF by treating IE with strong base such as lithium hydroxide, potassium hydroxide or sodium hydroxide

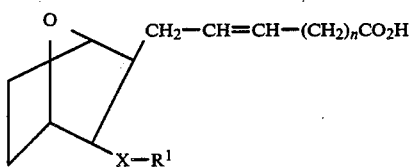
IF

In another method, compounds of the invention wherein X is O or S may be prepared starting with a cooled solution of the hemiacetal B

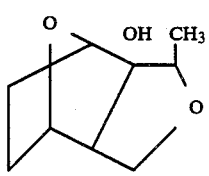
B in methylene chloride. Anhydrous $Na_2HPO_4$ is added and then a peracid solution (formed by adding trifluoroacetic anhydride to a mixture of hydrogen peroxide and methylene chloride) is added and the reaction is maintained for 1 to 2 days to form a crude oxidation product. To a slurry of lithium aluminum hydride in ether under argon is added the crude oxidation product formed above to form diol O

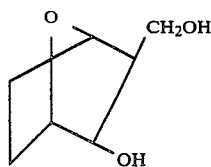

The diol O is tosylated by treating a solution of diol O, pyridine and methylene chloride cooled under argon with tosyl chloride in methylene chloride to form the tosylate P

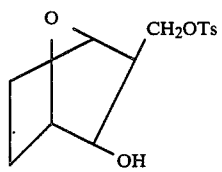

which is treated with p-TsOH and dihydropyran to form the tetrahydropyran ether Q

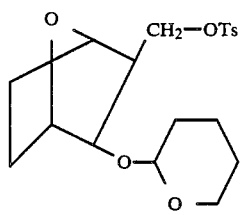

The tetrahydropyran ether Q is treated with a solution of sodium cyanide in dimethylsulfoxide to form the nitrile R

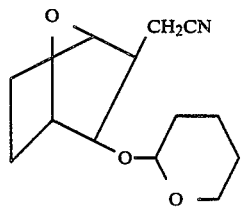

which is treated with diisobutyl aluminum hydride (DIBAL) to form the acetaldehyde S

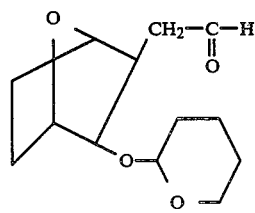

The acetaldehyde S is subjected to a Wittig rection employing carboxyalkyltriphenylphosphonium bromide [Br($C_6H_5$)$_3$P($CH_2$)$_n$COOH] in the presence of potassium t-amylate and an inert solvent such as toluene to form the vinyl acid T

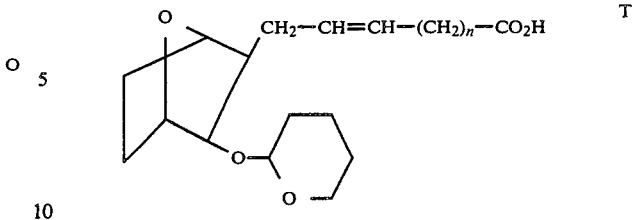

which is then treated with Amberlyst 15 resin in the presence of methanol to form the alcohol ester U

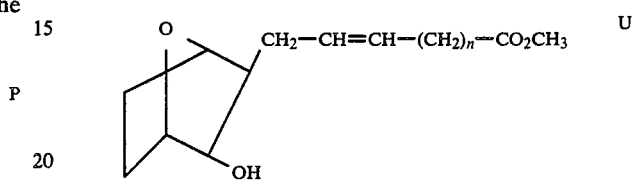

The alcohol ester U is treated with thiol acetic acid and a mixture of diisopropyl azo dicarboxylate (DIAD) and triphenyl phosphine in tetrahydrofuran to form the thioacetate V

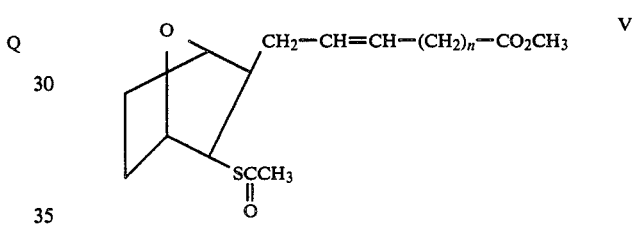

which together with a halo compound W (where X is S)

or with mesylate H (where X is O) is treated with strong base, such as NaOH, KOH or LiOH in an inert solvent such as xylene to form the ester IG

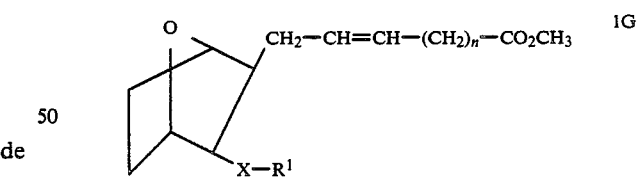

which may be hydrolyzed to the corresponding acid IH

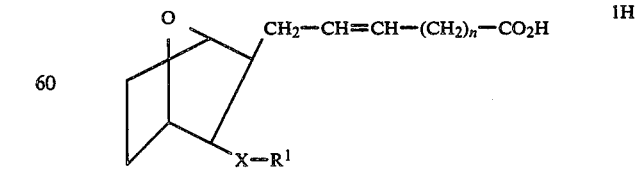

The cis form of compounds of the invention wherein X is S may also be prepared by adding a solution of alcohol ester U in methylene chloride to a solution of dimethyl sulfoxide in oxalyl chloride and methylene chloride under argon at a reduced temperature of from about −80° to about −70° C. After stirring for at least 30 minutes, triethyl amine or other organic base is added to form ketone X

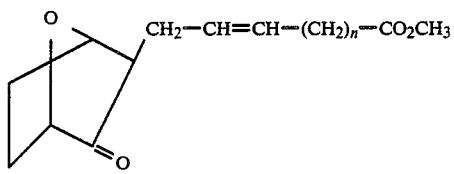

The ketone X dissolved in methyl alcohol is added to a solution of sodium borohydride in methyl alcohol to form the endo-alcohol Y

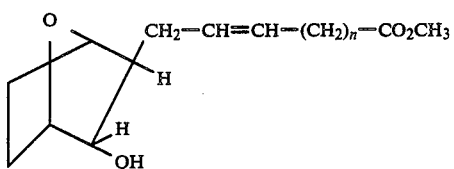

A solution of endo-alcohol Y in pyridine and methylene chloride is treated with mesyl chloride in methylene chloride to form the mesylate Z

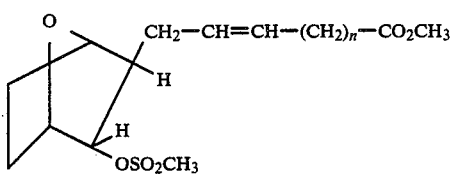

which is dissolved in tetrahydrofuran and added to a solution of mercaptan W in potassium t-butoxide in tetrahydrofuran under argon to form the cis ester II

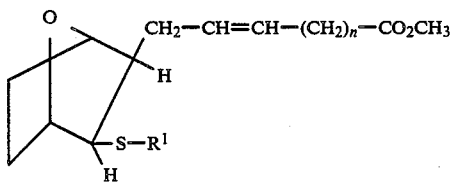

The cis ester II can be converted to the corresponding acid by hydrolysis by treating with an alkali metal hydroxide such as lithium, sodium or potassium hydroxide to form the corresponding alkali metal salt which is treated with strong acid such as hydrochloric acid to form the acid IJ

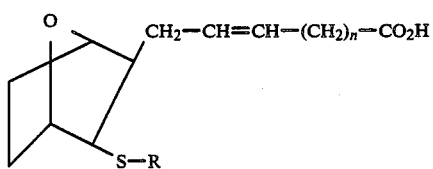

To form compounds wherein X is O or S and A is $(CH_2)_2$, compound IE, IF, IG, IH, II, or IJ is hydrogenated by treatment with hydrogen in the presence of a catalyst such as palladium/carbon and inert solvent such as ethyl acetate to form compound IK

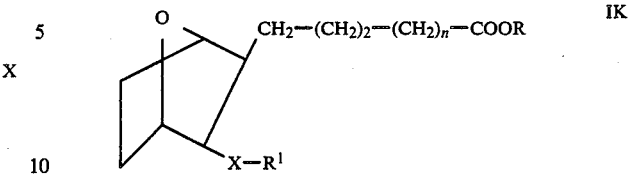

The starting lactone A may be prepared by hydrogenating the anhydride A′

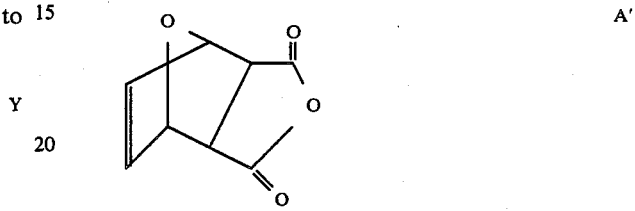

in the presence of a palladium catalyst and tetrahydrofuran to form the anhydride B′

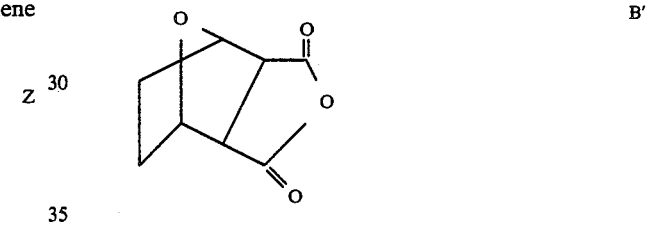

which may then be reduced by treating with sodium borohydride in the presence of tetrahydrofuran at reduced temperature to form lactone A.

To form compounds of formula I wherein X is

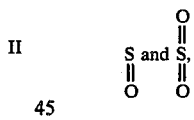

the sulfide derivative of formula I wherein X is S is subjected to an oxidation reaction, for example, by reacting same with sodium periodate, in the presence of methanol and tetrahydrofuran, to form the corresponding sulfinyl derivative

and sulfonyl derivative

The sulfinyl and sulfonyl derivatives may be separated by chromatography or other conventional separation procedures.

The tris(hydroxymethyl)aminomethane salt of any of the acids of formula I of the present invention is formed by reacting a solution of such acid in an inert solvent such as methanol with tris(hydroxymethyl)aminomethane and thereafter the solvent is removed by evaporation to leave the desired salt.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

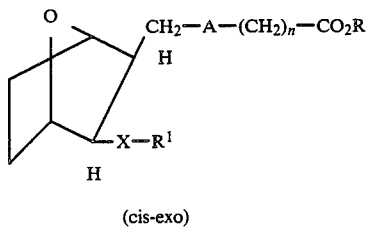

(cis-exo)

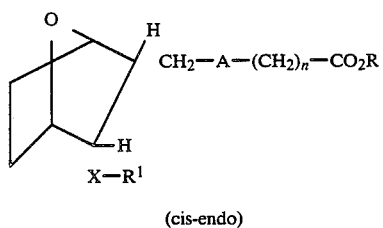

(cis-endo)

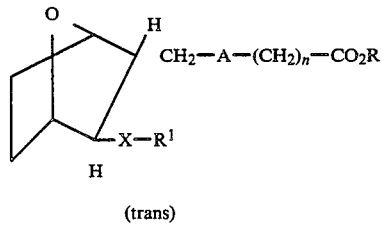

(trans)

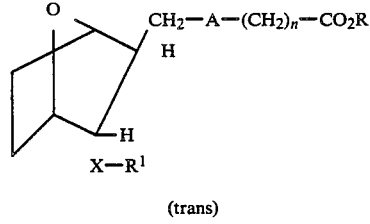

(trans)

The nucleus in each of the compounds of the invention is depicted as

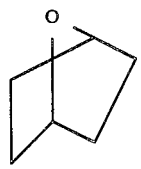

for matter of convenience; it will also be appreciated that the nucleus in the compounds of the invention may be depicted as

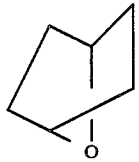

The compounds of this invention are cardiovascular agents useful as platelet aggregation inhibitors, such as inhibiting arachidonic acid-induced platelet aggregation (e.g., for treatment of thrombotic disease, such as inhibiting coronary or cerebral thromboses) and in inhibiting bronchoconstruction as induced by asthma. They are also selective thromboxane $A_2$ receptor antagonists, e.g., having a vasodilatory effect for treatment of myocardial ischemic disease, such as angina pectoris.

The compounds of the invention are also thromboxane synthetase inhibitors and thus may also be used for preventing gastrointestinal ulcer formation. They also increase the amount of endogenous prostacyclin $PGD_2$ and therefore may be used for controlling tumor cell metastasis or as antihypertensive agents.

The compounds of the invention are also arachidonic acid cyclooxygenase inhibitors.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

[1β,2α(Z),3β,4β]-7-[3-(Heptyloxy)-7-oxabicyclo[2.2.1-]hept-2-yl]-5-heptenoic acid, methyl ester

A.

[1β,2α,3α,4β]-(3-Acetyl-2-hydroxymethyl)-7-oxabicyclo[2.2.1]heptane

To a stirred solution of 5.0 g (32.5 mmol) of (3aα,4α,-7α,7aα)-hexahydro-4,7-epoxyiso-benzofuran-1(3H)-one (prepared as described in U.S. Pat. No. 4,143,054) in 360 ml of dry THF under argon at −78° C. was added dropwise 22 ml of 1.5M methyl lithium solution over a period of 15 minutes. The reaction mixture was stirred at −78° C. for 35 minutes and then quenched with 8 ml of acetone. The reaction mixture was concentrated in vacuo to approximately 100 ml and diluted with 300 ml of EtOAc and 300 ml of saturated NH$_4$Cl solution. The aqueous layer was saturated with NaCl and extracted with EtOAc (2×300 ml). The combined EtOAc extracts were dried (MgSO$_4$), filtered and concentrated in vacuo to give 3.82 g (72%) of title hemiketal, TLC: silica gel, 4% CH$_3$OH/CH$_2$Cl$_2$, R$_f$=0.54, Ce(SO$_4$)$_2$.

B.
[1β,2α,3α,4β]-(3-Acetyl-2-t-butyldimethylsiloxymethyl)-7-oxabicyclo[2.2.1]heptane To a stirred solution of 15 g (88.2 mmol) of Part A hemiketal in 267 ml of dry DMF under argon was added 35.5 g (521 mmol) of imidazole. To this mixture was then added 31.4 g (208 mmol) of t-butyldimethylsilyl chloride. The reaction mixture was stirred at room temperature for 21 hours. The reaction mixture was partitioned between 1.4 l of ether and 1.4 l of H$_2$O. The aqueous layer was extracted with ether (2×1.4 l). The combined ether extracts were dried (Na$_2$SO$_4$), filtered and concentrated in vacuo. The resultant oil was chromatographed on 180 g of silica gel 60 using 2:1 hexane-ether as eluant to give 25.0 g (99%) of title cis-ketone.

TLC:silica gel, 1:1 hexane-ether, R$_f$=0.56, Ce(SO$_4$)$_2$.

C.
[1β,2α,3β,4β]-(3-Acetyl-2-t-butyldimethylsilyloxymethyl)-7-oxabicyclo[2.2.1]heptane To a stirred solution of 25.0 g (87.8 mmol) of Part B cis-ketone in 1.12 l of CH$_3$OH was added 326 mg (8.15 mmol) of sodium methoxide under argon. The reaction mixture was stirred at room temperature for 22 hours. The reaction mixture was concentrated in vacuo to approximately 100 ml and diluted with 700 ml of EtOAc. The resulting solution was washed with saturated NaHCO$_3$ solution (2×100 ml) and brine (1×150 ml). The organic layer was dried (MgSO$_4$), filtered and concentrated in vacuo to give 24.5 g (98%) of title transketone.

TLC: silica gel, 2% CH$_3$OH in CH$_2$Cl$_2$, R$_f$=0.78,Ce(SO$_4$)$_2$. In subsequent runs, the conversion of starting lactone to Part C ketone was carried out without purification of any of the intermediates, A or B, in comparable yield.

D.
[1β,2α,3β,4β]-(3-Acetoxy-2-t-butyldimethylsilyloxymethyl)-7-oxabicyclo-[2.2.1]heptane and

E.
[1β,2α,3β,4β]-(3-Acetoxy-2-trifluoroacetoxymethyl)-7-oxabicyclo[2.2.1]heptane To a stirred slurry of 3.34 ml (138 mmol) of 90% H$_2$O$_2$ in 79 ml of dry CH$_2$Cl$_2$ at 0° C. was added dropwise 20.9 ml (149 mmol) of distilled trifluoroacetic anhydride over 20 minutes. This solution was stirred at 0° C. for 55 minutes. To a stirred slurry of 10.0 g (35.5 mmol) of Part C trans-ketone and 37.1 g of dry Na$_2$HPO$_4$ in 99 ml of dry CH$_2$Cl$_2$ at 0° C. was added the above peracid solution dropwise over 80 minutes. The resulting mixture was stirred at 0° C. for 5 hours and 30 minutes and then the solid (Na$_2$HPO$_4$) was removed by filtration. The filter cake was washed with CH$_2$Cl$_2$ (5×120 ml) and filtered. The filtrate was washed with 10% Na$_2$CO$_3$ solution (2×100 ml) and brine (1×200 ml). The organic layer was dried (MgSO$_4$), filtered and concentrated in vacuo. This was chromatographed on 182 g of silica gel 60 using 4:1 hexane-ether as eluant to give 2.96 g (28%) of Part D acetate 2.46 g (25%) of Part E acetate and 3.34 g of a mixture which contained the corresponding diol (>20%).

TLC: silica, hexane-ether 1:1, R$_f$(D), 0.70; (E), 0.60, Ce(SO$_4$)$_2$.

F.
[1β,2α,3β,4β]-(3-Acetoxy-2-hydroxymethyl)-7-oxabicyclo[2.2.1]heptane

To a stirred solution of 8.83 g (31.3 mmol) of Part E acetate in 100 ml of freshly distilled THF was added 20 ml of H$_2$O and 10 ml of saturated NaHCO$_3$ solution. The reaction mixture was stirred at room temperature for 6 hours and 20 minutes at which time an additional 10 ml of saturated NaHCO$_3$ solution was added. The mixture was stirred for 45 minutes and another 10 ml of saturated NaHCO$_3$ solution was added. The mixture was stirred for an additional 25 minutes and poured into 200 ml of brine. The aqueous layer was saturated with NaCl and extracted with ether (4×250 ml). The combined ether extracts were dried (MgSO$_4$), filtered and concentrated in vacuo to give 5.41 g of crude alcohol. Purification was effected by flash chromatography on 180 g of silica gel 60 using 3% CH$_3$OH/CH$_2$Cl$_2$ as eluant to give 5.22 g (90%) of title alcohol as an oil.

TLC: silica gel, 1:1 hexane-ether, R$_f$=0.24, Ce(SO$_4$)$_2$.

G.
[1β,2α,3β,4β]-(3-Acetoxy-2-methoxyethoxymethoxymethyl)-7-oxabicyclo[2.2.1]heptane To a stirred solution of 3.02 g (16.2 mmol) of Part F alcohol in 25 ml of dry CH$_2$Cl$_2$ under argon was added 5.66 ml (32.5 mmol) of diisopropyl ethyl amine, followed by dropwise addition of 2.78 ml (24.4 mmol) of 2-methoxyethoxymethyl chloride. The reaction mixture was stirred at room temperature for 21 hours and then diluted with 300 ml of CHCl$_3$. The organic layer was washed with 1N HCl solution (2×50 ml), saturated NaHCO$_3$ solution (1×100 ml). The organic layer was dried (MgSO$_4$), filtered and concentrated in vacuo. Purification was effected by flash chromatography on 150 g of silica gel 60 using 1% CH$_3$OH in CH$_2$Cl$_2$ as eluant to give 3.78 g (85%) of title G compound as an oil.

TLC: silica gel, 2% CH$_3$OH/CH$_2$Cl$_2$, R$_f$=0.25, Ce(SO$_4$)$_2$.

H.
[1β,2α,3β,4β]-(3-Heptyloxy-2-methoxyethoxymethoxymethyl)-7-oxabicyclo[2.2.1]heptane A mixture of 6.33 g (113 mmol) of powdered KOH in 170 ml of dry xylene was heated to reflux under argon atmosphere and 85 ml of xylene was removed by distillation. To this mixture was added a solution of 3.47 g (12.7 mmol) of title G compound in 115 ml of dry xylene. The volume of the reaction mixture was reduced 100 ml by distillative removal of xylene. To the reaction mixture was then added a solution of 12.3 g (67.3 mmol) of n-heptyl mesylate in 90 ml of dry xylene. The reaction mixture was refluxed for 3 hours. The cooled reaction mixture was diluted with 200 ml of brine and extracted with EtOAc (5×200 ml). The combined EtOAc extracts were dried (Na$_2$SO$_4$), filtered and concentrated in vacuo. This was chromatographed on 120 g of silica gel 60 using 1:1 hexane-ether as eluant to give 7.08 g of crude ether. Final purification was effected by flash chromatography on 103 g of silica gel 60 using 3:1 hexane-ether as eluant to give 3.0 g (72%) pure title ether.

TLC: silica gel 1:1 hexane-ether, R$_f$=0.45, Ce(SO$_4$)$_2$.

Anal. Calcd for C$_{18}$H$_{34}$O$_5$: C, 65.42; H, 10.37. Found: C, 64.87; H, 10.28.

I.
[1β,2α,3β,4β]-(3-Heptyloxy-2-hydroxymethyl)-7-oxabicyclo[2.2.1]heptane To a stirred solution of 1.9 g (5.76 mmol) of Part H-2-methoxyethoxymethyl ether in 25 ml of dry CH$_2$Cl$_2$ under argon at 0° C. was added dropwise 3.28 g (17.3 mmol) of TiCl$_4$. The reaction mixture was stirred for 30 minutes and quenched with 12 ml of concentrated NH$_4$OH solution. The reaction mixture was diluted with 120 ml of H$_2$O and extracted with EtOAc (5×100 ml). The combined EtOAc extracts were dried (MgSO$_4$), filtered and concentrated in vacuo. Purification was effected by flash chromatography on 80 g of silica gel 60 using 1% CH$_3$OH in CH$_2$Cl$_2$ as eluant to give 1.1 g (79%) of pure title heptyl ether alcohol as an oil.

TLC: silica gel, 4% CH$_3$OH/CH$_2$Cl$_2$, R$_f$=0.35, Ce(SO$_4$)$_2$.

Anal Calcd for C$_{14}$H$_{26}$O$_3$: C, 69.38; H, 10.81. Found: C, 69.04; H, 10.77.

J.
[1β,2α,3β,4β]-2-Formyl-3-(heptyloxy)-7-oxabicyclo[2.2.1]heptane

To a stirred mixture of 2.94 g (17.6 mmol) of pyridinium chlorochromate and 0.22 g. (2.73 mmol) of NaOAc in 55 ml of dry CH$_2$Cl$_2$ under argon at room temperature was added a solution of 1.32 g (5.45 mmol) of Part I heptyl ether alcohol in 16.5 ml of dry CH$_2$Cl$_2$ rapidly. The reaction mixture was stirred for 1 hour and 30 minutes and diluted with 72 ml of ether. The organic solution was decanted and the insoluble black residue was washed with ether (2×100 ml) until the precipitate became granular. The combined organic solution was passed through a 3″ pad of Florisil which was then washed with ether (3×100 ml). The combined filtrates were concentrated in vacuo to give 1.16 g (89%) of title aldehyde.

TLC: silica gel, 2% CH$_3$OH/CH$_2$Cl$_2$, R$_f$=0.34, Ce(SO$_4$)$_2$.

K.
[1β,2α,3β,4β]-3-(Heptyloxy)-2-(methoxyethenyl)-7-oxabicyclo[2.2.1]heptane To a stirred solution of 3.28 g (9.56 mmol) of methoxymethylenetriphenylphosphonium chloride in 45 ml of dry THF under argon in an acetone-ice bath was added 4.97 ml (7.11 mmol) of 1.43M Of potassium t-amylate solution dropwise over 10 minutes. To this mixture was added a solution of 1.13 g (4.71 mmol) of Part J aldehyde in 23 ml of dry THF dropwise at 0° C. over 70 minutes. The reaction mixture was stirred at room temperature for 2 hours, cooled in an acetone-ice bath, and then quenched with 20 ml of acetaldehyde. The reaction mixture was diluted with 150 ml of saturated NH$_4$Cl solution and 50 ml of 1N aqueous HCl solution and extracted with ether (3×270 ml). The combined ether extracts were dried (MgSO$_4$), filtered and concentrated in vacuo. Purification was effected by flash chromatography on 151 g of silica gel 60 using hexane-ether 7:1 as eluant to give 1.04 g (82%) of title vinyl ether as an oil.

TLC: silica gel, hexane-ether 2:1, R$_f$=0.60, Ce(SO$_4$)$_2$.

Anal Calcd for C$_{16}$H$_{28}$O$_3$: C, 71.60; H, 10.52. Found: C, 71.22; H, 10.34.

L.
[1β,2α,3β,4β]-2-(Formylmethyl)-3-(heptyloxy)-7-oxabicyclo[2.2.1]heptane To a stirred solution of 740 mg (2.76 mmol) of Part K vinyl ether in 7.4 ml of freshly distilled THF under argon was added 29.6 ml of 20% aqueous trifluoroacetic acid solution. The reaction mixture was stirred at room temperature for 3 hours and 10 minutes and then neutralized with solid NaHCO$_3$. The mixture was poured into 100 ml of H$_2$O and extracted with CH$_2$Cl$_2$ (4×80 ml). The combined CH$_2$Cl$_2$ extracts were dried (MgSO$_4$), filtered and concentrated in vacuo to give a colorless oil. This compound was dissolved in 30 ml of benzene and concentrated in vacuo to give 670 mg (95%) of pure title aldehyde as an oil.

TLC: silica gel, 1:1 hexane-ether, R$_4$=0.34, Ce(SO$_4$)$_2$.

M.
[1β,2α(Z),3β,4β]-7-[3-(Heptyloxy)-7-oxabicyclo[2.2.1]hept-2-yl]-5-heptenoic acid, methyl ester To a stirred solution of 1.96 g (4.43 mmol) of carboxybutyltriphenylphosphonium bromide in 35 ml of dry THF under argon at 0° C. was added dropwise 6.23 ml (7.91 mmol) of 1.27M of potassium t-amylate toluene solution. The mixture was stirred at 0° C. for an hour. To this homogeneous burgundy-red solution was added dropwise a solution of 670 mg (2.64 mmol) of Part L trans-aldehyde in 56 ml of dry THF over 80 minutes. The reaction mixture was allowed to warm to room temperature and stirred for 22 hours and 10 minutes. The reaction mixture was cooled in an ice-bath and quenched with dropwise addition of 10 ml of glacial acetic acid. The mixture was poured into 100 ml of brine and extracted with EtOAc (4×100 ml). The combined EtOAc extracts were dried (MgSO$_4$), filtered and concentrated in vacuo. The residue was treated with 300 ml of diazomethane solution and excess diazomethane was destroyed by addition of HOAc. The mixture was concentrated in vacuo and chromatographed on 40 g of silica gel 60 using 2:1 hexane-ether as eluant to give 900 mg of an impure mixture of title methyl ester and corresponding carboxylic acid. Purification was effected by flash chromatography on 141 g of silica gel 60 using hexane-ether 2:1 as eluant to give 350 mg (38%) of pure title methyl ester and 490 mg of a mixture of title methyl ester and corresponding carboxylic acid.

TLC: silica gel, hexane-ether 1:1, R$_f$=0.52, iodine.

EXAMPLE 2

[1α,2β(Z),3α,4α]-7-[3-(Heptyloxy)-7-oxabicyclo[2.2.1]hept-2-yl]-5-heptenoic acid To a stirred solution of 350 mg (1.00 mmol) of Example 1 methyl ester in 54 ml of freshly distilled THF and 9.0 ml of H$_2$O was added 10.0 ml of 1N aqueous lithium hydroxide solution. The reaction mixture was purged with argon vigorously for 30 minutes and stirred at room temperature for 8 hours and 20 minutes. The reaction mixture was acidified to pH 3 by the addition of 1N aqueous HCl solution and poured into 80 ml of brine. The aqueous layer was saturated with NaCl and extracted with EtOAc (4×100 ml). The combined EtOAc extracts were dried (MgSO4), filtered and concentrated in vacuo. Purification was effected by flash chromatography on 40 g of silica gel 60 using 2% CH3OH in CH2Cl2 as eluant to give 90 mg of pure title acid and 240 mg of a mixture of title acid and Example 1 methyl ester. The mixture was chromatographed on 24.2 g of silica gel 60 using 2% CH3OH/CH2Cl2 as eluant to give 210 mg of pure title acid. The total yield was 300 mg (89%).

TLC: silica gel, 1:1 hexane-ether, $R_f$=0.40, iodine.

Anal Calcd for $C_{20}H_{34}O_4$: C, 70.97; H, 10.12. Found: C, 70.67; H, 10.02.

EXAMPLE 3

[1β,2α(Z),3α,4β]-7-[3-(Heptyloxy)-7-oxabicyclo[2.2.1]hept-2-yl]-5-heptenoic acid

A.

[1β,2α,3α,4β]-2-Hydroxy-3-(hydroxymethyl)-7-oxabicyclo[2.2.1]heptane

A flask containing 250 ml of dry CH2Cl2 was cooled in an ice bath. To this was added 8.8 ml (364 mmol) of 90% H2O2. To this stirred slurry was added dropwise 58 ml (411 mmol) of trifluoroacetic anhydride over 40 minutes. During this time the pot temperature varied between 2°–7° C. The solution was stirred for an additional 25 minutes at 0° C.

A solution of 8.00 g (47.0 mmol) of crude hemiketal prepared as described in Example 1 Part A in 280 ml of CH2Cl2 was cooled to 0° C. and then 96.0 g (676 mmol) of anhydrous Na2HPO4 was added. To this mechanically stirred slurry was added the above peracid solution in 10 ml portions over 35 minutes. During the addition, the reaction mixture became thick but then thinned out again. The reaction was stirred at 0→2° C. for an additional 18 hours and then allowed to warm to room temperature and stirred for an additional 48 hours. At this time the reaction mixture was diluted with 100 ml CH2Cl2 and the solids were removed by filtration. The filter cake was washed with ~200 ml of ether and enough CH2Cl2 to afford ~1400 ml of filtrate. The filtrate was concentrated in vacuo to afford 18 g of crude oxidation product in the form of a colorless oil.

A slurry of 4.6 g (121 mmol) of LiAlH4 in 150 ml of ether under Ar was cooled in an ice bath. To this stirred slurry was added dropwise a solution of 18.0 g of crude oxidation product in 70 ml of ether. After 70 minutes, an additional 4.1 g (108 mmol) of LiAlH4 was added since the LiAlH4 in the flask had aggregated into a large ball. Thirty minutes later, the addition was complete and the flask was warmed to room temperature. After being stirred for 2.5 hours, the reaction mixture was diluted with 200 ml ether and then cooled in an ice bath. To this vigorously stirred mixture was added 8.5 ml of H2O dropwise over 30 minutes, followed by the sequential addition of 8.5 ml 15% NaOH and 25.5 ml H2O. This resulted in the formation of a white granular precipitate. The mixture was diluted with 100 ml EtOAc and filtered to remove solids. The filter cake was resuspended in 10% CH3OH in EtOAc (350 ml), stirred, and filtered. This washing procedure was repeated twice. The combined filtrates was concentrated in vacuo to afford 10.5 g of crude title diol. A 9.9 g portion of this material was chromatographed on 225 g of silica gel using 4% CH3OH/CH2Cl2 as eluant for fractions 1–60, followed by 500 ml of 6% MeOH/CH2Cl2 and 600 ml of 8% MeOH/CH2Cl2. This afforded 3.83 g (56%) of pure title diol, and 1.7 g of the monoacetate of the title diol. This acetate was subject to the above LiAlH4 reduction and chromatographed to afford an additional 13% yield of title diol. Total overall yield of title diol from starting hemiketal was 69%.

TLC: silica gel, 4% MeOH/CH2Cl2, $R_f$=0.14, iodine.

B.

[1β,2α,3α,4β]-2-Hydroxy-3-(p-tolsyloxymethyl)-7-oxabicyclo[2.2.1]heptane

A solution of 5.5 g (38.2 mmol) of Part A diol, 20 ml of pyridine, and 10 ml of dry CH2Cl2 was cooled to −20° C. under argon. To this stirred solution was added dropwise a solution of 8.23 g (43.2 mmol) of recrystallized TsCl in 25 ml of CH2Cl2 over a period of 30 minutes. The reaction mixture was stirred at −20° C. for 2 hours and then the flask was placed in the refrigerator (3°–5° C.) for 4 days. The flask was then allowed to warm to room temperature with stirring. The reaction mixture was partitioned between 300 ml of ether and 200 ml of 1N HCl. A precipitate began to form in the ether layer so a small amount (50–75 ml each) of EtOAc and MeOH was added which dissolved the precipitate. The organic layer was washed with 100 ml of 1N HCl. The combined aqueous layers were then extracted with 150 ml of ether. The combined organic layers were dried over MgSO4, filtered and concentrated in vacuo to give 11.7 g of white solid. This solid was stirred with approximately 75 ml of ether and then 25 ml of hexane was added. After chilling this mixture in the refrigerator for several hours, the white precipitate was collected and dried in vacuo to give 8.4 g (74%) of title compound, m.p. 132°–135° C.

TLC: silica gel, 2% MeOH/CH2Cl2, $R_f$=0.31, Ce(SO4)2.

C.

[1β,2α,3α,4β]-2-(2-Tetrahydropyranyloxy)-3-(p-tolsyloxymethyl)-7-oxabicyclo[2.2.1]heptane A solution of 8.2 g (27.5 mmol) of Part B compound in 130 ml of dry CH2Cl2 was cooled to 0° C. To this rapidly stirred solution was added 0.10 g of p-TsOH followed by dropwise addition of 4.0 ml (43.9 mmol) of dihydropyran. The flask was covered with foil and maintained at 0° C. After stirring for 4 hours, the reaction mixture was added to 100 ml of saturated NaHCO3 solution. The aqueous layer was extracted twice with 100 ml of CH2Cl2. The combined CH2Cl2 layers were dried over MgSO4, filtered and concentrated in vacuo to afford the crude product.

This was chromatographed on 180 g of silica gel using 4:1 hexane-ether as eluant for fractions 1–40, 2:1 hexane-ether for fraction 40–60 and ether for fractions 60→end. This afforded 7.2 g (69%) of pure title compound along with 1.26 g (12%) of slightly impure title compound, m.p. of fast moving isomer (FMI): 87°–94° C., softening at 82° C. (THP diastereomers).

TLC: silica gel, 1:1 hexane-ether, $R_f$=0.16, 0.24, Ce(SO4)2.

D.

[1β,2α,3α,4β]-2-(2-Tetrahydropyranyloxy)-3-(cyanomethyl)-7-oxabicyclo[2.2.1]heptane To a stirred solution of 7.0 g (18.3 mmol) of Part C compound in 70 ml of dry DMSO was added 5.95 g (121 mmol) of NaCN (powdered) and 0.12 g of NaHCO$_3$. This mixture was placed in a 95° C. oil bath for 4 hours. On cooling, the reaction mixture was partitioned between 500 ml of brine and 400 ml of ether. The aqueous layer was then extracted with three 400 ml portions of ether. The combined ether extracts were dried over MgSO$_4$, filtered and concentrated in vacuo to afford 5.4 g of crude product. Flash chromatography on 260 g of silica gel using 3:2 ether-hexane as eluant gave 4.2 g (97%) of title nitrile.

TLC: silica gel, 1:1 ether:hexane, R$_f$=0.12, Ce(SO$_4$)$_2$.

E.
[1β,2α,3α,4β]-2-(2-Tetrahydropyranyloxy)-3-(formylmethyl)-7-oxabicyclo[2.2.1]heptane A solution of 4.2 g (17.7 mmol) of Part D nitrile in 50 ml of dry toluene was cooled to −20° C. To this stirred solution was added dropwise 30 ml of 25% diisobutyl aluminum hydride (DIBAL) in toluene (44.6 mmol) over a period of 10 minutes. The bath temperature was maintained at −20° to −15° C. for 3½ hours. The reaction was then quenched at −20° C. by the addition of 30 ml of acetone, and then diluted with 250 ml of toluene. To this was added 100 g of silica gel followed by the dropwise addition of 10 ml of H$_2$O and 4.0 ml of glacial acetic acid. This slurry was stirred vigorously for 45 minutes at room temperature. The silica gel was removed and the cake washed with three 300 ml portions of acetone. The combined filtrates were concentrated in vacuo, redissolved in 100 ml ether and washed with 80 ml of half-saturated NaCl solution. The aqueous layer was back-extracted with 100 ml of ether. The combined ether layers were dried over Na$_2$SO$_4$, filtered and concentrated in vacuo to afford 3.8 g (89%) of title aldehyde.

TLC: silica gel; 1:1 hexane-ether, R$_f$=0.22, Ce(SO$_4$)$_2$.

F.
[1β,2α(Z),3α,4β]-7-[2-(2-Tetrahydropyranyloxy)-7-oxabicyclo[2.2.1]hept-2-yl]-5-heptenoic acid, methyl ester A slurry of 51.75 g (117 mmol) of carboxybutyltriphenylphosphonium bromide in 400 ml of THF was cooled in an ice bath under argon. To this stirred slurry was added dropwise 60 ml (84 mmol) of 1.4M potassium t-amylate toluene over a period of 48 minutes. At this point, the reaction mixture was allowed to warm to room temperature. The ylid solution was stirred at room temperature for 5½ hours at which time the addition of a solution of 3.7 g (15.4 mmol) of crude Part E aldehyde in 100 ml of THF was begun. The addition was complete after 55 minutes, and the resulting mixture was stirred at room temperature overnight. The mixture was cooled in an ice bath and quenched by the addition of a solution of 25 ml HOAc in 25 ml of toluene, followed by dilution with an additional 300 ml of toluene. The precipitate was removed by filtration and the filtrate was partitioned between 800 ml of half-saturated NaCl and 500 ml EtOAc (pH of aqueous layer was 3.5). The aqueous layer was then extracted with 3×500 ml of EtOAc. The combined organic layers were dried over MgSO$_4$, filtered, and concentrated in vacuo to give 12.6 g of crude product. This was triturated with iPr$_2$O/hexane. The filtrate was concentrated in vacuo to afford 8.8 g of crude acid. This was esterified with excess CH$_2$N$_2$ at 0° C. The resultant ester was chromatographed on 180 g of silica gel using 25% MeOH in CH$_2$Cl$_2$ as eluant. Fractions 46-62 were concentrated to afford 3.80 g (A) of pure title compound. Fractions 63-72 were concentrated to give 0.6 g (B) of a mixture of title compound and Ph$_3$P→O. Fractions 40-45 were concentrated to give 0.2 g (C) of a mixture of title compound and a faster-moving impurity.

TLC: silica gel, 4% MeOH/CH$_2$Cl$_2$, R$_f$=0.64, 0.71, (THP diastereomers), iodine.

G.
[1β,2α(Z),3α,4β]-7-[3-Hydroxy-7-oxabicyclo[2.2.1]hept-2-yl]-5-heptenoic acid, methyl ester Each portion of Part F compound was deprotected separately.

To a solution of 3.8 g (11.2 mmol) of Part F compound in 40 ml of MeOH was added 600 mg of crushed, dried Amberlyst 15 resin. This mixture was stirred vigorously for 4 hours at room temperature. It was then diluted with 100 ml of ether and filtered through a short pad of Celite. The filter cake was washed thoroughly with ether. The combined filtrates were concentrated in vacuo to afford crude title ester.

The other portions of Part F compound were deprotected using the same conditions; (0.2 g Part F(c)/5 ml MeOH/80 mg Amberlyst 15), (0.6 g (B)/5 ml MeOH/120 mg Amberlyst 15).

The crude products from Part F (A) and Part F (B) were combined and chromatographed on 110 g of silica gel using 2% MeOH/CH$_2$Cl$_2$ as eluant. This afforded 2.4 g (61% overall from starting Part E aldehyde) of pure title alcohol ester.

TLC: silica gel, 4% MeOH/CH$_2$Cl$_2$, R$_f$=0.34, iodine.

Anal Calcd for C$_{14}$H$_{22}$O$_4$: C, 66.12; H, 8.72. Found: C, 65.78; H, 8.66.

H.
[1β,2α(Z),3α,4β]-7-[3-(Heptyloxy)-7-oxabicyclo[2.2.1]hept-2-yl]-5-heptenoic acid A slurry of 0.42 g (7.5 mmol) of powdered KOH in 20 ml of xylene was heated to reflux under Ar and approximately 10 ml of xylene was removed by distillation. To this boiling solution was added a solution of 230 mg (0.91 mmol) of Part G alcohol, 1.00 g (5 mmol) of n-heptyl mesylate, and 5 ml of xylene. Approximately 3 ml of additional xylene was removed by distillation. TLC analysis after 20 minutes showed the reaction to be complete. The heat was removed and the reaction mixture was allowed to cool slowly.

On cooling, the reaction mixture was partitioned between 20 ml each of saturated NH$_4$Cl and EtOAc. The aqueous layer was acidified to pH=3.5 with 1N HCl and then extracted with 2×25 ml EtOAc. The combined EtOAc extracts were dried over MgSO$_4$, filtered and concentrated in vacuo to give the crude product. Chromatography on 35 g of silica gel using 4% MeOH/CH$_2$Cl$_2$ as eluant afforded 140 mg (46%) of title product along with 200 mg of impure title product.

TLC: silica gel, 4% CH$_3$OH/CH$_2$Cl$_2$, R$_f$=0.31, iodine.

Anal Calcd for C$_{20}$H$_{34}$O$_4$: C, 70.97; H, 10.12. Found: C, 71.15; H, 10.07.

EXAMPLE 4

[1β,2α(5Z),3β,4β]-7-[3-(Heptylthio)-7-oxabicyclo[2.2.1]hept-2-yl]-5-heptenoic acid, methyl ester and heptyl ester

A.

[1β,2α(5Z),3β,4β]-7-[3-(Acetylthio)-7-oxabicyclo[2.2.1]hept-2-yl]-5-heptenoic acid, methyl ester To a stirred solution of 1.56 g (5.95 mmol) of triphenylphosphine in 15 ml of THF at 0° C. was added 1.20 ml (6.09 mmol) of diisopropylazodicarboxylate over 7 minutes. This mixture was stirred at 0° C. for 30 minutes. To this mixture was then added dropwise over 10 minutes a solution of 520 mg (2.05 mmol) of Example 3 Part G alcohol and 0.75 ml (10.5 mmol) of thiolacetic acid in 5 ml of THF.

The reaction mixture was stirred at 0° C. for 1 hour and then allowed to warm to room temperature overnight. The resulting solution was concentrated in vacuo and the residue was triturated with 1:1 hexane-ether. The filtrate was concentrated in vacuo to afford a semisolid product. This was chromatographed on 100 g of silica gel using 2:1 hexane-ether as eluant followed by ether (fractions 61→69). This afforded 210 mg (33%) of pure title compound and 290 mg (56%) of recovered starting alcohol.

TLC: silica gel; 1:1 hexane-ether, $R_f$=0.45.

B.

[1β,2α(5Z),3β,4β]-7-[3-(Heptylthio)-7-oxabicyclo[2.2.1]hept-2-yl]-5-heptenoic acid, methyl ester and

C.

[1β,2α(5Z),3β,4β]-7-[3-(Heptylthio)-7-oxabicyclo[2.2.1]hept-2-yl]-5-heptenoic acid, heptyl ester A slurry of 0.50 g (8.93 mmol) of powdered KOH in 10 ml of xylene was heated to reflux. To this mixture was added a solution of 210 mg (0.67 mmol) of Part A compound and 0.70 ml (4.45 mmol) of heptyl bromide in 2 ml of xylene. The reaction mixture was refluxed for 3 hours and then an additional 1.1 ml (7.0 mmol) of heptyl bromide was added. After being allowed to reflux for an additional 30 minutes, the reaction mixture was allowed to cool to room temperature. The cooled reaction mixture was partitioned between 25 ml each of brine and ether. The aqueous layer was acidified by careful addition of 6N HCl pH≅4, was shaken with the ether layer, and separated. The aqueous layer was extracted with 25 ml ether. The combined ether extracts were dried over MgSO$_4$, filtered and concentrated in vacuo. The residue was esterified with excess ethereal CH$_2$N$_2$ at 0° C. The product was chromatographed on 38 g of silica gel using 4:1 hexane-ether as eluant. This afforded 0.06 g (20%) of title heptyl ester and 0.05 g (20%) of title methyl ester.

TLC: silica gel, 1:1 hexane-ether $R_f$(title methyl ester)=0.5; $R_f$(title heptyl ester)=0.75.

EXAMPLE 5

[1β,2α(5Z),3β,4β]-7-[3-(Heptylthio)-7-oxabicyclo[2.2.1]hept-2-yl]-5-heptenoic acid To a stirred solution of 60 mg Example 4 part C heptyl ester in 6.0 ml of freshly distilled THF and 1.0 ml of H$_2$O was added 2.0 ml of 1N LiOH solution. The mixture was purged with a stream of Ar for 30 minutes and then stirred at room temperature for 4.5 hours. At this time, TLC analysis showed that very little of Example 4 Part C heptyl ester had hydrolyzed so 1.0 ml of methanol was added, affording a nearly homogeneous solution. This was stirred at room temperature for 1.5 hours and then placed in the refrigerator overnight.

Part B methyl ester was hydrolyzed under the exact same conditions.

The two reaction mixtures were combined and partitioned between 40 ml each brine and ether. The aqueous layer was acidified to pH∼2 with 1N HCl and extracted with two 40 ml portions of ether. The combined organics were dried over MgSO$_4$, filtered and concentrated in vacuo to give 130 mg of crude product. Chromatography on 30 g of silica gel using 1:1 hexane-ether as eluant gave 34 mg (36%) of title acid.

TLC: silica gel, 4% MeOH/CH$_2$Cl$_2$, $R_f$=0.5.

Anal Calcd for C$_{20}$H$_{34}$O$_3$S: C, 67.80; H, 9.61; S, 9.04. Found: C, 67.54; H, 9.67; S, 8.84.

EXAMPLE 6

[1β,2α(5Z),3α,4β]-7-[3-(Heptylthio)-7-oxabicyclo[2.2.1]hept-2-yl]-5-heptenoic acid, methyl ester

A.

[1α,2α(5Z),3α,4β]-7-[3-oxo-7-oxabicyclo[2.2.1]hept-2-yl]-5-heptenoic acid, methyl ester To a solution of 1.12 g (8.86 mmol) of oxalyl chloride in 15 ml of dry CH$_2$Cl$_2$ at −78° C. under argon atmosphere was added 1.38 g (17.7 mmol) of dry DMSO over 10 minutes. To this mixture was added a solution of 1.50 g (5.91 mmol) of Example 3 Part G alcohol in 30 ml of dry CH$_2$Cl$_2$ dropwise over 20 minutes. The reaction mixture was stirred for 65 minutes and then 4.56 g (45.1 mmol) of triethyl amine was added dropwise. The resulting mixture was allowed to warm to room temperature and stirred for 35 minutes. The mixture was then diluted with 500 g of ether and washed with 1N aqueous HCl solution (3×125 ml), saturated NaHCO$_3$ solution (1×125 ml) and brine (1×200 ml). The solution was dried over anhydrous MgSO$_4$, filtered and concentrated in vacuo to give 1.49 g (100%) of title ketone as an oil.

TLC: silica gel, hexane-ether 1:1, $R_f$=0.54, Ce(SO$_4$)$_2$.

B.

[1β,2α(5Z),3β,4α]-7-[3-Hydroxy-7-oxabicyclo[2.2.1]hept-2-yl]-5-heptenoic acid, methyl ester To a stirred solution of 0.23 g (6.13 mmol) of NaBH$_4$ in 80 ml CH$_3$OH at 0° C. under argon was added a solution of 1.49 g (5.91 mmol) of Part A ketone in 80 ml of CH$_3$OH dropwise. The reaction mixture was stirred for 65 minutes and then quenched by the addition of 3 ml of acetone. This mixture was concentrated in vacuo to about 20 ml and diluted with 300 ml of ether. The resulting solution wash washed once with 150 ml of 1N aqueous HCl solution. The aqueous layer was saturated with NaCl and extracted with ether (2×300 ml). The combined ether extracts were dried over anhydrous Na$_2$SO$_4$, filtered and concentrated in vacuo. This was chromatographed on 80 g of silica gel 60 using ether-hexane 3:1 as eluant to give 1.06 g (72%) of title endo-alcohol as an oil. TLC: silica gel, ether-hexane 2:1, $R_f$=0.24, Ce(SO$_4$)$_2$.

C.

[1β,2α(5Z),3β,4α]-7-[3-Mesyloxy-7-oxabicyclo[2.2.1-]hept-2-yl]-5-heptenoic acid, methyl ester To a stirred solution of 900 mg (3.54 mmol) of Part B endo-alcohol in 18 ml of dry pyridine at 0° C. under argon was added a solution of 1.63 g (14.2 mmol) of mesyl chloride in 18 ml of dry $CH_2Cl_2$. This mixture was allowed to warm to room temperature and stirred for 7 hours. The mixture was diluted with 700 ml of ether and washed with 1N HCl (2×180 ml), saturated $NaHCO_3$ solution (1×150 ml) and brine (1×200 ml). The ether solution was dried over anhydrous $Na_2SO_4$, filtered and concentrated in vacuo. Purification was effected by flash chromatography on 47 g of silica gel 60 using hexane-ether 1:1 as eluant to give 1.12 g (86%) of title mesylate as an oil.

TLC: silica gel, hexane-ether 1:2, $R_f=0.30$, $Ce(SO_4)_2$.

D.

[1β,2α(5Z),3α,4β]-7-[3-(Heptylthio)-7-oxabicyclo[2.2.1]hept-2-yl]-5-heptenoic acid, methyl ester To a stirred solution of 134 mg (1.05 mmol) of potassium t-butoxide in 1 ml of dry THF under argon was added 0.36 ml (2.11 mmol) of heptyl mercaptan.

To this mixture was added a solution of 100 mg (0.30 mmol) of Part C mesylate in 1 ml of dry THF. The reaction mixture was diluted with 2 ml of dry DMSO and heated at 95° C. for 6 hours and 20 minutes. The cooled reaction mixture was diluted with 30 ml of half-saturated NaCl solution and extracted with 40 ml of ether. The aqueous layer was acidified to pH 4.5 by the addition of 1N aqueous HCl solution and extracted with ether (3×40 ml). The combined ether extracts were washed with 20 ml of water, dried ($MgSO_4$), filtered and concentrated in vacuo. The residue was treated with etheral diazomethane at room temperature and the excess diazomethane was destroyed by the addition of glacial HOAc. Concentration in vacuo gave the crude product. Purification was effected by flash chromatography on 30 g of silica gel 60. A stepped solvent gradient was used for elution; hexane (120 ml), 4:1 hexane-ether (120 ml), 2:1 hexane-ether (120 ml), 1:1 hexane-ether (120 ml) and finally 2:1 ether-hexane. This gave 28.7 mg (25.6%) of title thioether, 38.1 mg (38.1%) of recovered starting Part C mesylate and 19.6 mg (25.9%) of Part B endo-alcohol.

TLC=silica gel, hexane-ether 1:2, $R_f=0.66$, $Ce(SO_4)_2$.

EXAMPLE 7

[1β,2α(5Z),3α,4β]-7-[3-(Heptylthio)-7-oxabicyclo[2.2.1]hept-2-yl]-5-heptenoic acid To a stirred solution of 101 mg (0.27 mmol) of Example 6 methyl ester in 12.9 ml of freshly distilled THF was added 2.5 ml of $H_2O$ and 2.9 ml of 1N aqueous lithium hydroxide solution. The reaction mixture was purged with argon vigorously for 15 minutes and stirred at room temperature for 8 hours and 30 minutes. Another batch of 25 mg of methyl ester was hydrolyzed separately in the same manner and then combined for work-up. The combined reaction mixtures were acidified to pH 3 by the addition of 1N aqueous HCl solution and poured into 70 ml of brine. The resulting solution was saturated with NaCl and extracted with EtOAc (4×100 ml). The combined EtOAc extracts were dried ($Na_2SO_4$), filtered and concentrated in vacuo to give 200 mg of crude product as an oil. Purification was effected by flash chromatography on 30 g of silica gel 60 using hexane-ether 1:1 as eluant to give 42 mg (35%) of pure title acid. TLC=silica gel, hexane-ether 1:1, $R_f=0.26$, $I_2$.

Anal Calcd for $C_{20}H_{34}O_3S$: C, 67.75; H, 9.67; S, 9.04. $C_{20}H_{34}O_3S\cdot0.35$ mole·$H_2O$: C, 66.58; H, 9.69; S, 8.90. Found: C, 66.49; H, 9.57; S, 8.73.

EXAMPLE 8

(1β,2α,3α,4β)-7-[3-([Heptyloxy)-7-oxabicyclo[2.2.1-]heptyl-2-yl]heptanoic acid

A.

(1β,2α,3α,4β)-7-[3-Hydroxy-7-oxabicyclo[2.2.1]hept-2-yl]heptanoic acid, methyl ester To 760 mg (3.0 mmol) of Example 3, part G alcohol ester dissolved in 60 ml of ethyl acetate is added, under an argon atmosphere, 160 mg of 5% Pd on carbon. The argon atmosphere is exchanged for a slight positive pressure of hydrogen and the reaction is stirred for 8 hours at 25°, filtered through a Celite plug and is evaporated to provide the title A compound.

B.

(1β,2α,3α,4β)-7-[3-([Heptyloxy)-7-oxabicyclo[2.2.1-]heptyl-2-yl]heptanoic acid

Following the procedure of Example 3, part H except substituting the Part A alcohol ester for the Example 3G alcohol ester, the title product is obtained.

EXAMPLE 9

[1β,2α(Z),3α,4β]-7-[3-(Phenyloxy)-7-oxabicyclo[2.2.1-]hept-2-yl]-5-heptenoic acid (a) Phenol (1 mmol) is added to a solution of triphenylphosphine (1 mmol), diethylazodicarboxylate (1 mmol) and title B alcohol from Example 6 (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give [1β,2α(Z),-3α,4β]-7-[3-(phenyloxy)-7-oxabicyclo[2.2.1-]hept-2-yl]-5-heptenoic acid, methyl ester.

(b) Following the procedure as set out in Example 1 Part H, the ester from part (a) is converted to the title compound.

EXAMPLE 10

(1β,2α,3α,4β)-7-[3-(Phenyloxy)-7-oxabicyclo[2.2.1-]hept-2-yl]heptanoic acid

Following the procedure of Examples 6, 8 and 9 except substituting the Example 9 compound for the Example 2 compound in Example 8, the title compound is obtained.

EXAMPLE 11

[1β,2α(Z),3α,4β]-7-[3-[(7-Phenyl-3-heptenyl)thio]-7-oxabicyclo[2.2.1]hept-2-yl]-5-heptenoic acid Following the procedure of Examples 6 and 7 except substituting 7-phenyl-3-heptenylthio for heptylmercaptan, the title compound is obtained.

EXAMPLE 12

(1β,2α,3α,4β)-7-[3-[(6-Hexenyl)thio]-7-oxabicyclo[2.2.1]hept-2-yl]heptanoic acid Following the procedure of Examples 6, 7 and 8 except substituting 6-hexenylthiol for heptylmercaptan, the title compound is obtained.

EXAMPLE 13

[1β,2α(Z),3α,4β]-7-[3-[(7-Heptynyl)thio]-7-oxabicyclo[2.2.1]hept-2-yl]-5-heptenoic acid Following the procedure of Examples 6 and 7 except substituting 7-heptynylthiol for heptylmercaptan, the title compound is obtained.

EXAMPLE 14

[1β,2α(Z),3β,4β]-7-[3-(Propyloxy)-7-oxabicyclo[2.2.1]hept-2-yl]-5-heptenoic acid Following the procedure of Examples 1 and 2 substituting propyl mesylate for n-heptyl mesylate, the title compound is obtained.

EXAMPLE 15

[1α,2β(Z),3α,4α]-7-[3-(Phenyloxy)-7-oxabicyclo[2.2.1]hept-2-yl]-5-heptenoic acid Following the procedure of Example 9 except substituting Example 3G alcohol ester for Example 6B alcohol, the title compound is obtained.

EXAMPLE 16

[1α,2β(Z),3α,4α]-7-[3-(Benzyloxy)-7-oxabicyclo[2.2.1]hept-2-yl]-5-heptenoic acid Following the procedure of Examples 1 and 2 except substituting benzyl mesylate for n-heptyl mesylate, the title compound is obtained.

EXAMPLE 17

[1α,2β(Z),3α,4α]-7-[3-(Cyclohexyloxy)-7-oxabicyclo[2.2.1]hept-2-yl]-5-heptenoic acid Following the procedures of Examples 1 and 2 except substituting cyclohexyl mesylate for n-heptyl mesylate, the title compound is obtained.

EXAMPLE 18

[1α,2β(Z),3α,4α]-7-[3-(Cyclopentylmethyloxy)-7-oxabicyclo[2.2.1]hept-2-yl]-5-heptenoic acid Following the procedures of Examples 1 and 2 except substituting cyclopentylmethyl mesylate for n-heptyl mesylate, the title compound is obtained.

EXAMPLE 19

[1α,2β(Z),3α,4α]-7-[3-(2,3-Dimethyl-2-heptenyloxy)-7-oxabicyclo[2.2.1]hept-2-yl]-5-heptenoic acid Following the procedure of Examples 1 and 2 except substituting 2,3-dimethyl-2-heptenyl mesylate for n-heptyl mesylate, the title compound is obtained.

EXAMPLE 20

[1α,2β(Z),3α,4α]-7-[3-(6-Heptynyloxy)-7-oxabicyclo[2.2.1]hept-2-yl]-5-heptenoic acid Following the procedure of Examples 1 and 2 except substituting 6-heptynyl mesylate for n-heptyl mesylate, the title compound is obtained.

EXAMPLE 21

[1β,2α(Z),3α,4β]-7-[3-(Octyloxy)-7-oxabicyclo[2.2.1]hept-2-yl]-5-heptenoic acid

Following the procedure of Example 3 except substituting octyl mesylate for n-heptyl mesylate, the title compound is obtained.

EXAMPLE 22

[1β,2α(Z),3α,4β]-7-[3-(Phenylpropoxy)-7-oxabicyclo[2.2.1]hept-2-yl]-5-heptenoic acid Following the procedure of Example 3 except substituting phenyl propyl mesylate for n-heptyl mesylate, the title compound is obtained.

EXAMPLE 23

[1β,2α(Z),3α,4β]-7-[3-(Cyclohexyloxy)-7-oxabicyclo[2.2.1]hept-2-yl]-5-heptenoic acid Following the procedure of Example 3 except substituting cyclohexyl mesylate for n-heptyl mesylate, the title compound is obtained.

EXAMPLE 24

[1β,2α(Z),3α,4β]-7-[3-(Cyclopentylethyloxy)-7-oxabicyclo[2.2.1]hept-2-yl]-5-heptenoic acid Following the procedure of Example 3 except substituting cyclopentylethyl mesylate for n-heptyl mesylate, the title compound is obtained.

EXAMPLE 25

[1β,2α(Z),3α,4β]-7-[3-(2-Propenyloxy)-7-oxabicyclo[2.2.1]hept-2-yl]-5-heptenoic acid Following the procedure of Example 3 except substituting 2-propenyl mesylate for n-heptyl mesylate, the title compound is obtained.

EXAMPLE 26

[1β,2α(Z),3α,4β]-7-[3-(6-Heptynyloxy)-7-oxabicyclo[2.2.1]hept-2-yl]-5-heptenoic acid Following the procedure of Example 3 except substituting 6-heptynyl mesylate for n-heptyl mesylate, the title compound is obtained.

EXAMPLE 27

(1α,2β,3β,4α)-7-[3-(Pentyloxy)-7-oxabicyclo[2.2.1]hept-2-yl]heptanoic acid

Following the procedure of Examples 3 and 8 except substituting pentyl mesylate for n-heptyl mesylate, the title compound is obtained.

EXAMPLE 28

(1α,2β,3β,4α)-7-[3-(Benzyloxy)-7-oxabicyclo[2.2.1]hept-2-yl]heptanoic acid

Following the procedure of Examples 3 and 8 except substituting benzyl mesylate for n-heptyl mesylate, the title compound is obtained.

EXAMPLE 29

(1α,2β,3β,4α)-7-[3-(Cyclopentyloxy)-7-oxabicyclo[2.2.1]hept-2-yl]heptanoic acid

Following the procedure of Examples 3 and 8 except substituting cyclopentyl mesylate for n-heptyl mesylate, the title compound is obtained.

EXAMPLE 30

(1α,2β,3β,4α)-7-[3-(Cyclohexylmethyloxy)-7-oxabicyclo[2.2.1]hept-2-yl]heptanoic acid Following the procedure of Examples 3 and 8 except substituting cyclohexylmethyl mesylate for n-heptyl mesylate, the title compound is obtained.

EXAMPLE 31

(1α,2β,3β,4α)-7-[3-(3-Ethyl-3-octenyloxy)-7-oxabicyclo[2.2.1]hept-2-yl]heptanoic acid Following the procedure of Examples 3 and 8 except substituting 3-ethyl-3-octenyl mesylate for n-heptyl mesylate, the title compound is obtained.

EXAMPLE 32

(1α,2β,3β,4α)-7-[3-(5-Octynyloxy)-7-oxabicyclo[2.2.1]hept-2-yl]heptanoic acid

Following the procedure of Examples 3 and 8 except substituting 5-octynyl mesylate for n-heptyl mesylate, the title compound is obtained.

EXAMPLE 33

[1β,2α(Z),3β,4β]-7-[3-(Butylthio)-7-oxabicyclo[2.2.1]hept-2-yl]-5-heptenoic acid Following the procedure of Examples 4 and 5 except substituting butylbromide for n-heptyl bromide, the title compound is obtained.

EXAMPLE 34

[1β,2α(Z),3β,4β]-7-[3-(Benzylthio)-7-oxabicyclo[2.2.1]hept-2-yl]-5-heptenoic acid Following the procedure of Examples 4 and 5 except substituting benzylbromide for n-heptylbromide, the title compound is obtained.

EXAMPLE 35

[1β,2α(Z),3β,4β]-7-[3-(Cyclopentylthio)-7-oxabicyclo[2.2.1]hept-2-yl]-5-heptenoic acid Following the procedure of Examples 4 and 5 except substituting cyclopentylbromide for n-heptylbromide, the title compound is obtained.

EXAMPLE 36

[1β,2α(Z),3β,4β]-7-[3-(Cyclohexylmethylthio)-7-oxabicyclo[2.2.1]hept-2-yl]-5-heptenoic acid Following the procedure of Examples 4 and 5 except substituting cyclohexylmethylbromide for n-heptylbromide, the title compound is obtained.

EXAMPLE 37

[1β,2α(Z),3β,4β]-7-[3-(4-Pentenylthio)-7-oxabicyclo[2.2.1]hept-2-yl]-5-heptenoic acid Following the procedure of Examples 4 and 5 except substituting 4-pentenylbromide for n-heptylbromide, the title compound is obtained.

EXAMPLE 38

[1β,2α(Z),3β,4β]-7-[3-(3-Heptynylthio)-7-oxabicyclo[2.2.1]hept-2-yl]-5-heptenoic acid Following the procedure of Examples 4 and 5 except substituting 3-heptynylbromide for n-heptylbromide, the title compound is obtained.

EXAMPLE 39

[1β,2α(Z),3α,4β]-7-[3-(Nonylthio)-7-oxabicyclo[2.2.1]hept-2-yl]-5-heptenoic acid Following the procedure of Examples 6 and 7 except substituting nonylthiol for n-heptanethiol, the title compound is obtained.

EXAMPLE 40

[1β,2α(Z),3α,4β]-7-[3-(Phenylthio)-7-oxabicyclo[2.2.1]hept-2-yl]-5-heptenoic acid Following the procedure of Examples 6 and 7 except substituting phenylthiol for n-heptanethiol, the title compound is obtained.

EXAMPLE 41

[1β,2α(Z),3α,4β]-7-[3-(Phenethylthio)-7-oxabicyclo[2.2.1]hept-2-yl]-5-heptenoic acid Following the procedure of Examples 6 and 7 except substituting phenethylthiol for n-heptanethiol, the title compound is obtained.

EXAMPLE 42

[1β,2α(Z),3α,4β]-7-[3-(Cyclohexylthio)-7-oxabicyclo[2.2.1]hept-2-yl]-5-heptenoic acid Following the procedure of Examples 6 and 7 except substituting cyclohexylthiol for n-heptanethiol, the title compound is obtained.

EXAMPLE 43

[1β,2α(Z),3α,4β]-7-[3-(Cyclopentylmethylthio)-7-oxabicyclo[2.2.1]hept-2-yl]-5-heptenoic acid Following the procedure of Examples 6 and 7 except substituting cyclopentylmethylthiol for n-heptanethiol, the title compound is obtained.

EXAMPLE 44

[1β,2α(Z),3α,4β]-7-[3-(2-Butenylthio)-7-oxabicyclo[2.2.1]hept-2-yl]-5-heptenoic acid Following the procedure of Examples 6 and 7 except substituting 2-butenylthiol for n-heptanethiol, the title compound is obtained.

EXAMPLE 45

[1β,2α(Z),3α,4β]-7-[3-(5-Hexynylthio)-7-oxabicyclo[2.2.1]hept-2-yl]-5-heptenoic acid Following the procedure of Examples 6 and 7 except substituting 5-hexynylthiol for n-heptanethiol, the title compound is obtained.

EXAMPLE 46

(1β,2α,3α,4β)-7-[3-(Propylthio)-7-oxabicyclo[2.2.1]hept-2-yl]heptanoic acid

Following the procedure of Examples 6, 7 and 8 except substituting propylthiol for n-heptanethiol, the title compound is obtained.

EXAMPLE 47

(1β,2α,3α,4β)-7-[3-(Phenylthio)-7-oxabicyclo[2.2.1]hept-2-yl]heptanoic acid

Following the procedure of Examples 6, 7 and 8 except substituting phenylthio for n-heptanethiol, the title compound is obtained.

EXAMPLE 48

[1β,2α(Z),3α,4β]-7-[3-(3-Methylbenzylthio)bicyclo[2.2.1]hept-2-yl]-5-heptenoic acid Following the procedure of Examples 6 and 7 except substituting 3-methylbenzylthiol for n-heptanethiol, the title compound is obtained.

EXAMPLE 49

(1β,2α,3α,4β)-7-[3-(Cyclohexylthio)-7-oxabicyclo[2.2.1]hept-2-yl]heptanoic acid

Following the procedure of Examples 6, 7 and 8 except substituting cyclohexylthiol for n-heptanethiol, the title compound is obtained.

EXAMPLE 50

(1β,2α,3α,4β)-7-[3-(Cycloheptylmethylthio)-7-oxabicyclo[2.2.1]hept-2-yl]heptanoic acid Following the procedure of Examples 6, 7 and 8 except substituting cycloheptylmethylthiol for n-heptanethiol, the title compound is obtained.

EXAMPLE 51

(1β,2α,3α,4β)-7-[3-(2-Pentenylthio)-7-oxabicyclo[2.2.1]hept-2-yl]heptanoic acid

Following the procedure of Examples 6, 7 and 8 except substituting 2-pentenylthiol for n-heptanethiol, the title compound is obtained.

EXAMPLE 52

(1β,2α,3α,4β)-7-[3-(4-Pentynylthio)-7-oxabicyclo[2.2.1]hept-2-yl]heptanoic acid

Following the procedure of Examples 6, 7 and 8 except substituting 4-pentynylthiol for n-heptanethiol, the title compound is obtained.

It will also be appreciated that the carboxybutyl triphenylphosphonium bromide of the structure $$Br(C_6H_5)_3P(CH_2)_3-COOH$$

employed in forming the upper side chain in the aforementioned examples may be replaced by $$Br(CH_6H_5)_3P(CH_2)_n COOH$$

wherein $(CH_2)_n$ is defined hereinbefore, to form compounds of the invention wherein the upper side chain is of the structure $$-CH_2-A-(CH_2)_n-COOR.$$

EXAMPLES 53 TO 67

Following the procedures outlined in the specification and described in the above working Examples, the following compounds may be prepared.

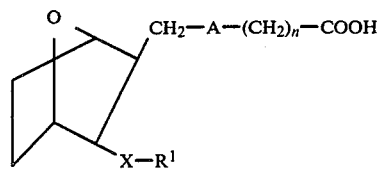

| Ex. No. | A | n | X | q | R¹ |
|---|---|---|---|---|---|
| 53. | $(CH_2)_2$ | 0 | O | — | 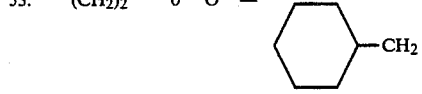 |
| 54. | $(CH_2)_2$ | 2 | S | 2 |  |
| 55. | CH=CH | 4 | S | 0 | 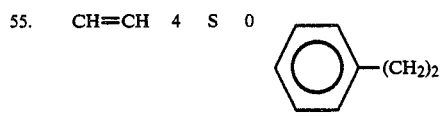 |
| 56. | $(CH_2)_2$ | 6 | O | — | $C_9H_{19}$ |
| 57. | CH=CH | 8 | S | 2 | $C_7H_{15}$ |
| 58. | $(CH_2)_2$ | 0 | S | 2 | $C_2H_5$ |
| 59. | $(CH_2)_2$ | 1 | S | 1 | $CH_3$ |
| 60. | CH=CH | 3 | O | — | 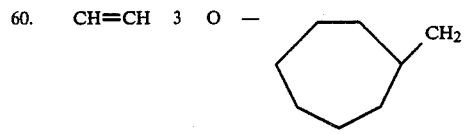 |
| 61. | $(CH_2)_2$ | 5 | S | 0 | 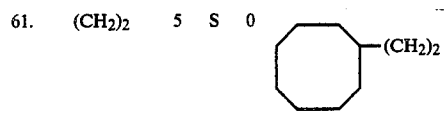 |
| 62. | $(CH_2)_2$ | 7 | S | 0 | $C_6H_5$ |
| 63. | $(CH_2)_2$ | 0 | O | — | 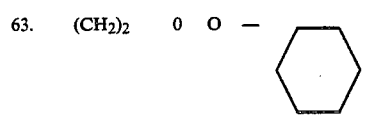 |
| 64. | CH=CH | 0 | S | 2 | 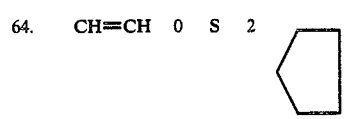 |
| 65. | CH=CH | 2 | S | 0 | 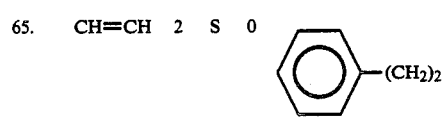 |
| 66. | $(CH_2)_2$ | 3 | O | — | 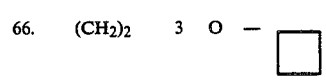 |
| 67. | $(CH_2)_2$ | 4 | S | 2 | $CH_3CH=CH-CH_2-$ |

What is claimed is:
1. A compound of the structure

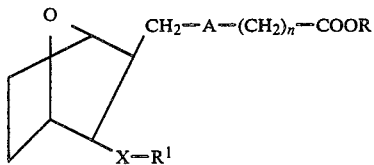

including all stereoisomers thereof, wherein
A is —CH=CH— or —CH₂—CH₂—;
n is 0 to 8;
X is O or

wherein
q is 0, 1 or 2;
R is H, lower alkyl, alkali metal or tris(hydroxymethyl)aminomethane; and
R¹ is lower alkyl, aryl, arylalkyl, cycloalkyl, cycloalkylalkyl, lower alkenyl containing 2 to 12 carbons or lower alkynyl containing 2 to 12 carbons, wherein lower alkyl or alkyl alone or as part of another group contains 1 to 12 carbons and is unsubstituted or is substituted with halo, hydroxy, alkylamino, alkylthio, CF₃, alkoxy, aryl, alkyl-aryl, haloaryl, cycloalkyl or alkylcycloalkyl;
aryl alone or as part of another group contains 6 to 10 carbons in the ring portion and is unsubstituted or is substituted with 1 or 2 lower alkyl groups, 1 or 2 halogens, aryl, 1 or 2 hydroxy groups, 1 or 2 lower alkoxy groups, 1 or 2 alkylamino groups or 1 or 2 alkylthio groups;
cycloalkyl alone or as part of another group contains 3 to 12 carbons and is unsubstituted or is substituted with 1 or 2 halogens, 1 or 2 lower alkyl groups and/or 1 or 2 lower alkoxy groups, 1 or 2 hydroxyl groups, 1 or 2 alkylamino groups, an aryl group, or 1 or 2 alkylthio groups; and
(CH₂)ₙ may contain 1 or 2 lower alkyl or halo substituents.

2. The compound as defined in claim 1 wherein X is O.

3. The compound as defined in claim 1 wherein X is S.

4. The compound as defined in claim 1 wherein n is 3 to 5.

5. The compound as defined in claim 1 wherein A is CH=CH, n is 3 to 5, R is H and R¹ is lower alkyl.

6. The compound as defined in claim 1 wherein R¹ is heptyl including all isomers thereof.

7. The compound as defined in claim 1 having the name [1α,2β(Z),3α,4α]-7-[3-(heptyloxy)-7-oxabicyclo[2.2.1]hept-2-yl]-5-heptenoic acid or the methyl ester thereof including all stereoisomers thereof.

8. The compound as defined in claim 1 having the name [1β,2α(Z),3α,4β]-7-[3-(heptyloxy)-7-oxabicyclo[2.2.1]hept-2-yl]-5-heptenoic acid including all stereoisomers thereof.

9. The compound as defined in claim 1 [1β,2α(5Z),3β,4β]-7-[3-(heptylthio)-7-oxabicyclo[2.2.1]hept-2-yl]-5-heptenoic acid or the methyl ester or heptyl ester thereof, including all stereoisomers thereof.

10. The compound as defined in claim 1 having the name [1β,2α(5Z),3α,4β]-7-[3-(heptylthio)-7-oxabicyclo[2.2.1]hept-2-yl]-5-heptenoic acid or the methyl ester thereof, including all stereoisomers thereof.

11. A method of inhibiting arachidonic acid-induced platelet aggregation and broncho-constriction, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

14. A method of inhibiting platelet aggregation or inhibiting bronchoconstriction associated with asthma, which comprises administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,608,386

DATED : August 26, 1986

INVENTOR(S) : Steven E. Hall et al.

It is certified that error appears in the above-identified patent and that said Letters Patent is hereby corrected as shown below:

Column 2, line 42, "or" first occurrence, should read --on--.
Column 3 line 56, structure B should read

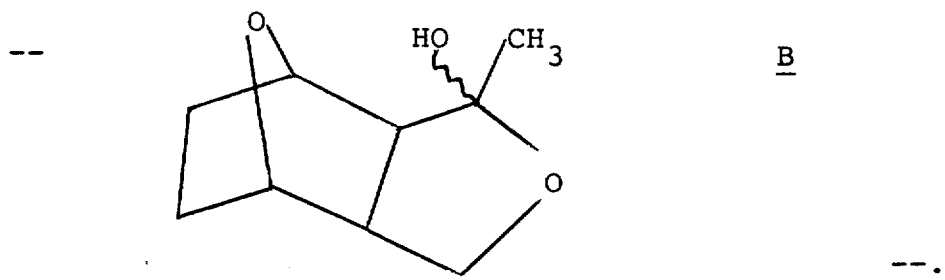

Column 6, line 1, structure M should read

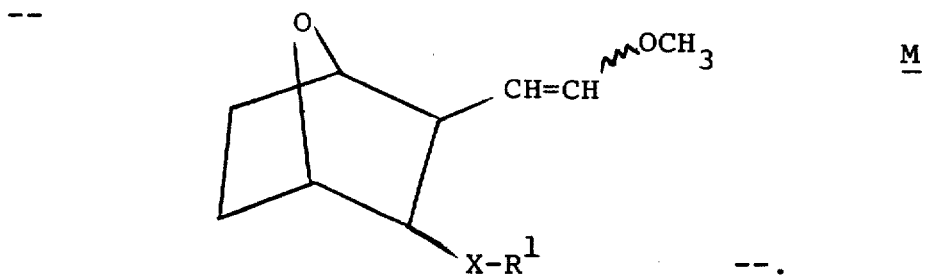

UNITED STATES PATENT AND TRADEMARK OFFICE
CERTIFICATE OF CORRECTION

PATENT NO. : 4,608,386  
DATED : August 26, 1986  
INVENTOR(S) : Steven E. Hall et al.

Page 2 of 4

It is certified that error appears in the above-identified patent and that said Letters Patent is hereby corrected as shown below:

Column 6, line 55, structure B should read

-- 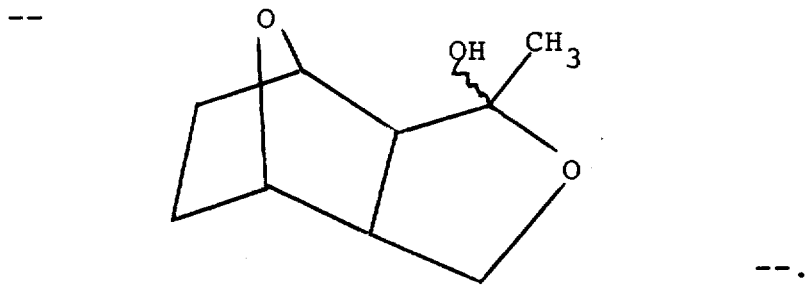 --.

Column 11, lines 20-55, structures Ia, Ib, Ic and Id should read

-- 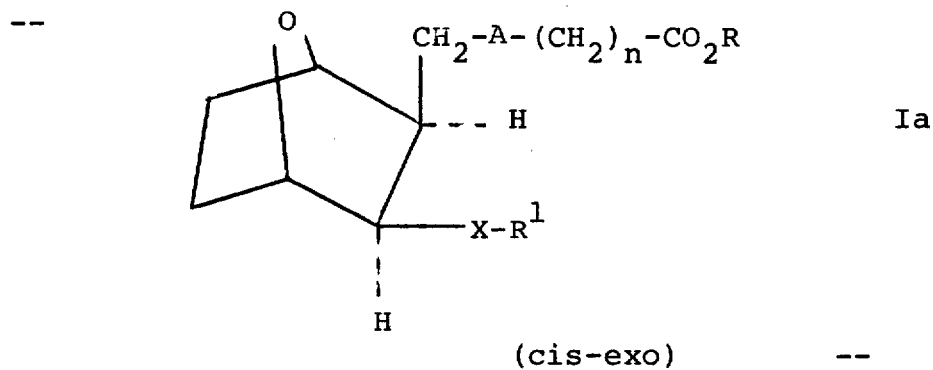

Ia (cis-exo) --

UNITED STATES PATENT AND TRADEMARK OFFICE
CERTIFICATE OF CORRECTION

PATENT NO. : 4,608,386
DATED : August 26, 1986
INVENTOR(S) : Steven E. Hall et al.

It is certified that error appears in the above-identified patent and that said Letters Patent is hereby corrected as shown below:

--
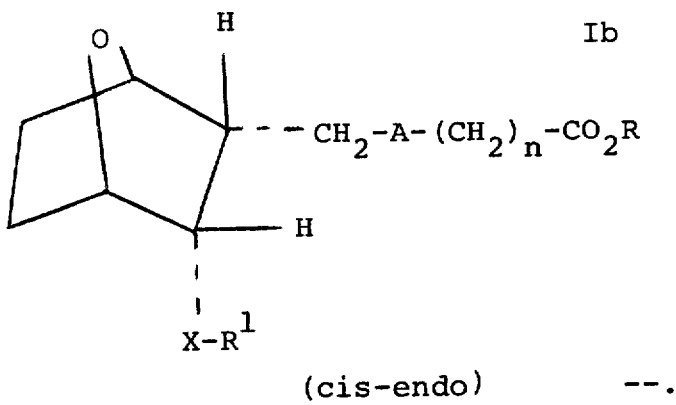
(cis-endo) --.

--
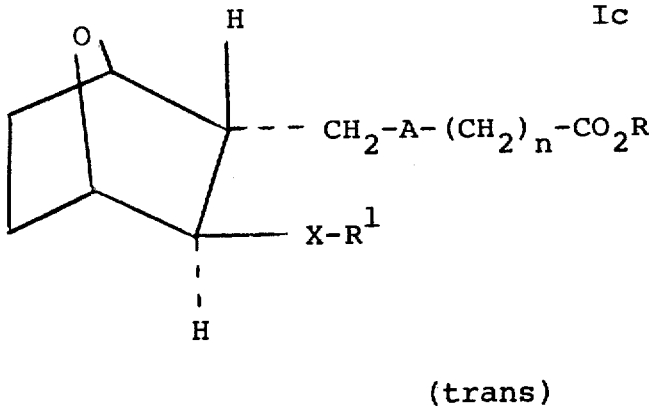
(trans)

UNITED STATES PATENT AND TRADEMARK OFFICE
CERTIFICATE OF CORRECTION

PATENT NO. : 4,608,386                    Page 4 of 4

DATED     : August 26, 1986

INVENTOR(S) : Steven E. Hall et al.

It is certified that error appears in the above-identified patent and that said Letters Patent is hereby corrected as shown below:

-- 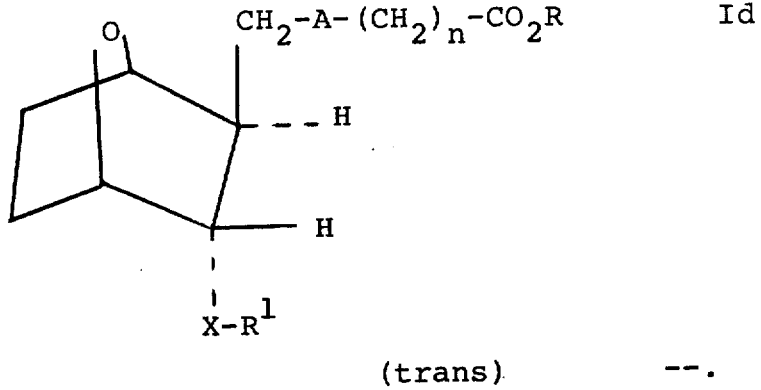        Id (trans)           --.

Signed and Sealed this

Ninth Day of December, 1986

Attest:

DONALD J. QUIGG

Attesting Officer          Commissioner of Patents and Trademarks